United States Patent
Hong et al.

(10) Patent No.: US 10,711,245 B2
(45) Date of Patent: Jul. 14, 2020

(54) DIRECT CONVERSION METHOD OF HUMAN FIBROBLASTS INTO NEURAL STEM CELLS USING SMALL MOLECULES

(71) Applicant: KOREA UNIVERSITY RESEARCH AND BUSINESS FOUNDATION, Seoul (KR)

(72) Inventors: Sung Hoi Hong, Seoul (KR); Kyung-Ah Choi, Gangwon-do (KR); In Sik Hwang, Seoul (KR)

(73) Assignee: INSTEMCARE INC., Seoul (KR)

( * ) Notice: Subject to any disclaimer, the term of this patent is extended or adjusted under 35 U.S.C. 154(b) by 0 days.

(21) Appl. No.: 15/545,314

(22) PCT Filed: Apr. 12, 2016

(86) PCT No.: PCT/KR2016/003819
§ 371 (c)(1),
(2) Date: Jul. 20, 2017

(87) PCT Pub. No.: WO2016/167528
PCT Pub. Date: Oct. 20, 2016

(65) Prior Publication Data
US 2018/0010094 A1    Jan. 11, 2018

(30) Foreign Application Priority Data

Apr. 13, 2015 (KR) .................. 10-2015-0051993
Apr. 11, 2016 (KR) .................. 10-2016-0044187

(51) Int. Cl.
*C12N 5/0797* (2010.01)
*A61K 35/30* (2015.01)

(52) U.S. Cl.
CPC ............ *C12N 5/0623* (2013.01); *A61K 35/30* (2013.01); *C12N 2500/30* (2013.01); *C12N 2500/38* (2013.01); *C12N 2500/46* (2013.01); *C12N 2501/11* (2013.01); *C12N 2501/115* (2013.01); *C12N 2501/999* (2013.01); *C12N 2506/1307* (2013.01)

(58) Field of Classification Search
None
See application file for complete search history.

(56) References Cited

U.S. PATENT DOCUMENTS

| 2014/0038291 A1* | 2/2014 | Ahlfors ................. C12N 15/85 435/441 |
| 2015/0030570 A1 | 1/2015 | Pan et al. |
| 2016/0041149 A1* | 2/2016 | Lindquist ........... G01N 33/5058 514/152 |

FOREIGN PATENT DOCUMENTS

| CN | 103561751 A | 2/2014 |
| CN | 104278008 A | 1/2015 |
| JP | 2011135864 A | 7/2011 |
| JP | 2011521639 A | 7/2011 |
| JP | 2012507264 A | 3/2012 |
| JP | 2014503194 A | 2/2014 |
| JP | 2015509719 A | 4/2015 |
| KR | 10-2007-0089018 A | 8/2007 |
| KR | 10-2011-0124106 A | 11/2011 |
| KR | 10-2013-0085767 A | 7/2013 |
| KR | 20130085767 | * 10/2013 |
| WO | WO2014069479 A1 | 9/2016 |

OTHER PUBLICATIONS

Grochowski et al Clinical Neurology and Neurosurgery 173 (2018) 8-1410.*
Oikawa, H., "Dream of Chemistry in the 21st Century", "Genome Resource Chemistry", 2011, pp. 62-65, vol. 16, No. 5.
Oikawa, H., "Dream of Chemistry in the 21st Century", "Genome Resource Chemistry", 2011, Page(s) Machine Translation, vol. 16, No. 5.
Tan, F., et al., "Inhibition of Transforming Growth Factor Beta (TGF-Beta) Signaling Can Substitute for Oct4 Protein in Reprogramming and Maintain Pluripotency", "Journal of Biological Chemistry", Feb. 13, 2015, pp. 4500-4511, vol. 290, No. 7.
Zhang, Y., et al., "Small Molecules, Big Roles—the Chemical Manipulation of Stem Cell Fate and Somatic Cell Reprogramming", "Journal of Cell Science", 2012, pp. 5609-5620, vol. 125, No. 23.
Cheng, L., et al., "Generation of neural progenitor cells by chemical cocktails and hypoxia", "Cell Research", Mar. 18, 2014, pp. 665-679, vol. 64.
De Carvalho, D. D., et al., "DNA Methylation and Cellular Reprogramming", "Trends in Cell Biology", Oct. 2010, pp. 609-617, vol. 20, No. 10.
Groszer, M., et al., "Negative Regulation of Neural Stem/Progenitor Cell Proliferation by the Pten Tumor Suppressor Gene in Vivo", "Science", Dec. 7, 2001, pp. 2186-2189, vol. 294.
Tojo, M., et al., "The ALK-5 inhibitor A-83-01 inhibits Smad signaling and epithelial-to-mesenchymal transition by transforming growth factor-", "Cancer Science", Nov. 2005, pp. 791-800, vol. 96, No. 11.

(Continued)

*Primary Examiner* — Blaine Lankford
(74) *Attorney, Agent, or Firm* — Hultquist, PLLC; Steven J. Hultquist

(57) ABSTRACT

The present invention relates to a method of converting human fibroblasts into neural stem cells, and more particularly, to a method of directly converting human fibroblasts into neural stem cells using only a combination of small-molecule compounds without any introduction of a foreign gene, and to the use of the neural stem cells. The method of directly converting human fibroblasts into neural stem cells using only small-molecule compounds without any introduction of a foreign gene makes it possible to obtain genetically stable neural stem cells in an amount sufficient for use in cell therapy by deriving them from human fibroblasts. The neural stem cells obtained according to the method of the present invention can differentiate into functional neural cells and are not tumorigenic. Thus, these neural stem cells are useful as cellular therapeutic agents for treatment of brain diseases.

11 Claims, 11 Drawing Sheets
(6 of 11 Drawing Sheet(s) Filed in Color)

(56) References Cited

OTHER PUBLICATIONS

Xi, G., et al., "Induced Neural Stem Cells Generated from Rat Fibroblasts", "Genomics Proteomics Bioinformatics", Sep. 27, 2013, pp. 312-319, vol. 11.

A. Hotta, "Small Molecule Control of IPS Cells", "The Trends of Arts and Sciences", 2011, pp. 62-65, vol. 16, No. 5.

A. Hotta, "Small Molecule Control of IPS Cells", "The Trend of Arts and Sciences", 2011, Page(s) English Translation, vol. 16, No. 5.

Bernal, A., et al., "Nestin-Expressing Progenitor Cells: Function, Identify and Therapeutic Implications", "Cellular and Molecular Life Sciences", 2018, pp. 2177-2195, vol. 75.

Dahlstrand, J., et al., "Characterization of the Human Nestin Gene Reveals a Close Evolutionary Relationship to Neurofilaments", "Journal of Cell Science", 1992, pp. 589-597, vol. 103.

Dahlstrand, J., et al., "Nestin mRNA Expression Correlates with the Central Nervous System Progenitor Cell State in Many, But Not All, Regions of Developing Central Nervous System", "Developmental Brain Research", 1995, pp. 109-129, vol. 84.

Glazer, R.I., et al., "Musashi1: A Stem Cell Marker No Longer in Search of a Functiion", "Cell Cycle", Sep. 1, 2008, pp. 2635-2639, vol. 7, No. 17.

Hawes, S.M., et al., "Identification and Maintenance of Cell Lineage Progenitors Derived From Human ES Cells", "Handbook of Stem Cells", 2004, pp. 501-510, vol. 1.

Kaneko, Y., et al., "Musashi1: An Evolutionarily Conserved Marker for CNS Progenitor Cells Including Neural Stem Cells", "Developmental Neuroscience", 2000, pp. 139-153, vol. 22.

Lendahl, U., et al., "CNS Stem Cells Express a New Class of Intermediate Filament Protein", "Cell", Feb. 23, 1990, pp. 585-595, vol. 60.

Maslov, A.Y., et al., "Neural Stem Cell Detection, Characterization, and Age-Related Changes in the Subventricular Zone of Mice", "The Journal of Neuroscience", Feb. 18, 2004, pp. 1726-1733, vol. 24, No. 7.

Nitta, K.R., et al., "Expression of Sox1 During Xenopus Early Embryogenesis", "Biochemical and Biophysical Research Communications", 2006, pp. 287-293, vol. 351.

Okano, H., et al., "Function of RNA-Binding Protein Musashi-1 in Stem Cells", "Experimental Cell Research", 2005, pp. 349-356, vol. 306.

Pevny, L.H., et al., "A Role for SOX1 in Neural Determination", "Development", 1998, pp. 1967-1978, vol. 125.

Sakakibara, S., et al., "Mouse-Musashi1, a Neural RNA-Binding Protein Highly Enriched in the Mammalian CNS Stem Cell", "Developmental Biology", 1996, pp. 230-242, vol. 176.

Venere, M., et al., "Sox1 Marks an Activated Neural Stem/Progenitor Cell in the Hippocampus", "Development", 2012, pp. 3938-3949, vol. 139.

Wiese, C., et al., "Nestin Expression—a Property of Multi-Lineage Progenitor Cells?", "CMLS, Cell. Mol. Life Sci.", 2004, pp. 2510-2522, vol. 61.

Higuchi, A., et al., "Generation of Pluripotent Stem Cells Without the Use of Genetic Material", "Laboratory Investigation", 2015, pp. 26-42, vol. 95.

Shahbazi, M., et al., "Inhibitory effects of neural stem cells derived from human embryonic stem cells on differentiation and function of monocyte-derived dendritic cells", "Journal of Neurological Sciences", 2013, pp. 85-93, vol. 330, Publisher: Elsevier.

* cited by examiner

DIRECT CONVERSION METHOD OF HUMAN FIBROBLASTS INTO NEURAL STEM CELLS USING SMALL MOLECULES

CROSS-REFERENCE TO RELATED APPLICATIONS

This application is a U.S. national phase under the provisions of 35 U.S.C. § 371 of International Patent Application No. PCT/KR2016/003819 filed Apr. 12, 2016, which in turn claims priority of Korean Patent Application No. 10-2015-0051993 filed Apr. 13, 2015 and Korean Patent Application No. 10-2016-0044187 filed Apr. 11, 2016. The disclosures of such international patent application and Korean priority patent applications are hereby incorporated herein by reference in their respective entireties, for all purposes.

TECHNICAL FIELD

The present invention relates to a method of converting human fibroblasts into neural stem cells, and more specifically, to a method of directly converting human fibroblasts into neural stem cells using only a combination of small-molecule compounds without any introduction of a foreign gene.

BACKGROUND ART

There has been rapidly increasing interest in reprogramming, since a study indicating the production of induced pluripotent stem cells from human fibroblasts was reported in 2007. Human embryonic stem cells used in previous stem cell studies have problems in that they pose ethical issues by the use of human embryos, cause immune rejection, and form a teratoma when undifferentiated embryonic stem cells are transplanted. Furthermore, adult stem cells have problems in that they are difficult to obtain and the differentiation potential thereof is limited. However, induced pluripotent stem cells avoid ethical issues and have no immune rejection, but may cause problems associated with teratoma formation when undifferentiated stem cells are transplanted. Although induced pluripotent stem cells have properties similar to those of embryonic stem cells, viral systems that are mainly used to form induced pluripotent stem cells may cause mutations by random integration of genes. In order to overcome the problem of viral systems, plasmids, proteins, RNAs or the like are used, but they have low efficiency, and may cause new problems due to the use of oncogenes.

In attempts to overcome the problems of such induced pluripotent stem cells, studies on direct conversion of human fibroblasts into desired cells using direct conversion method have been reported. Among them, direct conversion into neural cells using fibroblasts for the treatment of intractable brain diseases has been actively conducted, and the study for generation of neural cells were successful through various combination of neuron-related transcription factors have been introduced into human fibroblasts. These studies demonstrated their potential for use as cellular therapeutic agents against intractable brain diseases, but there was difficulty in obtaining neural cells in amounts sufficient for use in cell therapy, because neural cells are already differentiated cells.

Due to this problem, in recent years, methods for allowing fibroblasts to directly differentiate into neural stem cells have been studied. Most methods induce neural stem cells from fibroblasts by introducing various transcription factors using the viral system, however, in more recent, it has reached a level that can induce neural stem cells using only single transcription factor. Neural stem cells are self-renewable, and thus can be obtained in desired amounts, and are capable of differentiating into neural cells. Furthermore, neural stem cells derived from fibroblasts of each individual by direct conversion pose no ethical issues, have no immune rejection, and do not induce tumorigenesis after transplantation. Thus, induced neural stem cells are very useful as cellular therapeutic agents against intractable brain diseases.

Cell therapy is a therapeutic method that transplants experimentally derived healthy cells to replace damaged cells and tissues in the human body. In the case of patients having diseases caused by genetic factors, skin cells may be directly converted into desired cells, and the desired cells may be transplanted after abnormal genes therein are replaced with normal genes by genetic manipulation. However, because direct conversion methods that have been studied before are methods that introduce foreign genes, cells obtained by these methods are difficult to actually use as cellular therapeutic agents.

Accordingly, the present inventors have made extensive efforts to induce neural stem cells from fibroblasts using small-molecule compounds without any introduction of a foreign gene, and as a result, have found that neural stem cells can be produced which are capable of proliferating in a sufficient amount required for transplantation and which are genetically stable (genomic DNA stability) without inducing tumorigenesis, thereby completing the present invention.

DISCLOSURE OF INVENTION

Technical Problem

It is an object of the present invention to provide a method for producing neural stem cells, as a cellular therapeutic agent for treating brain disease, by culturing human fibroblasts in a medium containing small molecule compounds.

Technical Solution

To achieve the above object, the present invention provides a method for producing neural stem cells, comprising a step of culturing human fibroblasts in a medium containing Thiazovivin, Valproic acid, Purmorphamine, A8301, SB431542 and CHIR99021.

The prevent invention also provides a cellular therapeutic agent for treating brain disease, which contains neural stem cells produced by the above-described method.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION FOR CARRYING OUT THE INVENTION

Figure 1:
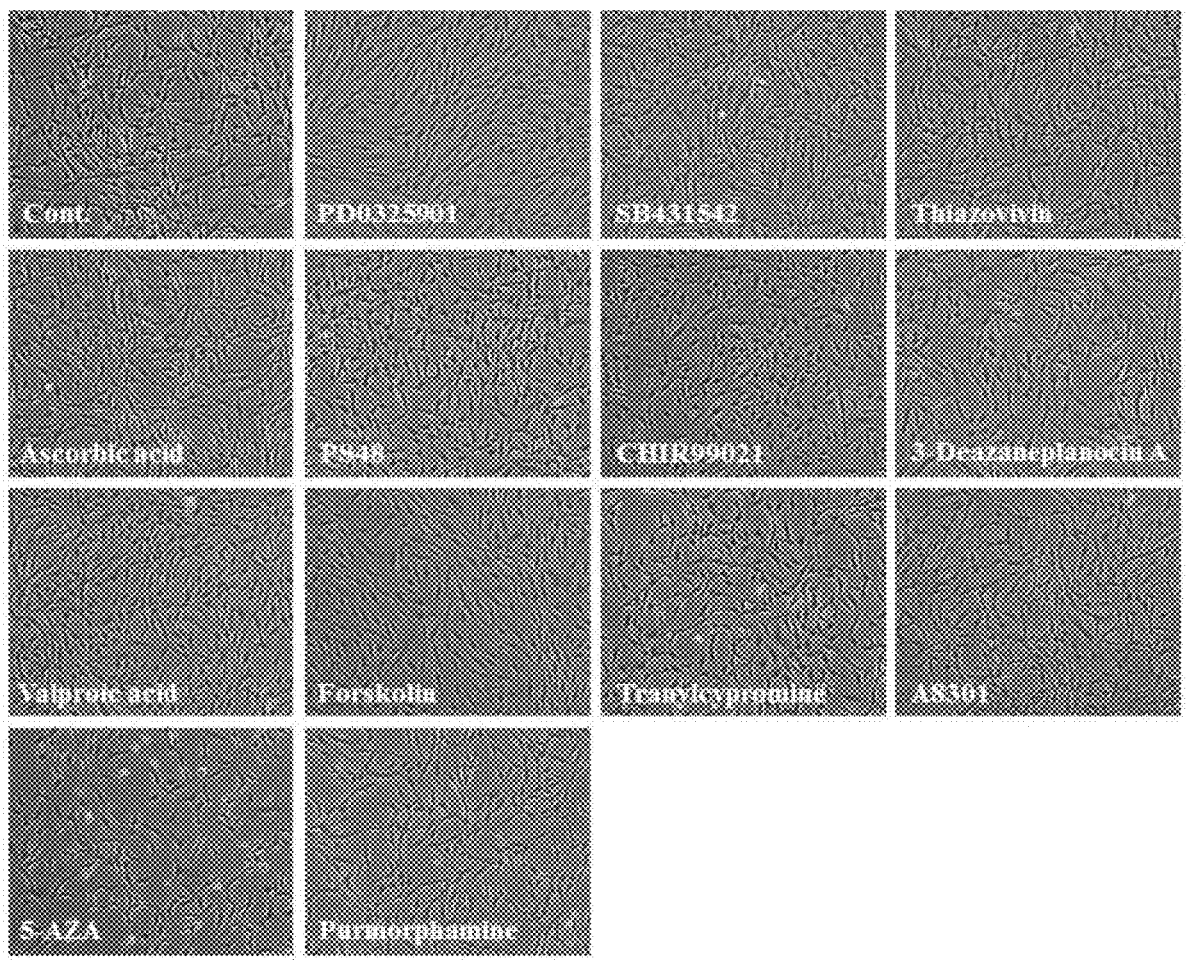
FIG. 1 shows the results of observing cellular morphological changes following addition of 13 different small-molecule compounds.

Unless defined otherwise, all technical and scientific terms used herein have the same meaning as commonly understood by one of ordinary skill in the art to which the invention pertains. Generally, the nomenclature used in this invention and the experiment methods, which will be described below, are those well-known and commonly employed in the art.

In the present invention, an optimal combination of small-molecule compounds for deriving neural stem cells from human fibroblasts was established, and the function of each of various small-molecule compounds was examined. As a result, human neural stem cells were derived from human fibroblasts by using a culture medium containing a combination of small-molecule compounds, and neural stem cells with genetic stability without chromosomal abnormality were obtained, and optimized culture conditions for growing and maintaining fibroblast-derived neural stem cells were also established during a long period of time. Then, the fundamental characteristics of human neural stem cells were examined, and the ability of human neural stem cells to differentiate into three major types of neural cells and various types of neural cells was confirmed. Furthermore, it has been found that fibroblast-derived human neural stem cells differentiate into three major types of neural cells without tumorigenesis after transplantation. In addition, it has been found that some of small-molecule compounds regulate expressions of endoderm- and mesoderm-specific genes, indicating that they have the potential to derive endodermal and mesodermal cells.

Therefore, in one aspect, the present invention is directed to a method for producing neural stem cells, comprising a step of culturing human fibroblasts in a medium containing Thiazovivin, Valproic acid, Purmorphamine, A8301, SB431542 and CHIR99021.

"Thiazovivin (N-benzyl-2-(pyrimidin-4-ylamino)thiazole-4-carboxamide)" that is used in the present invention is known to block the Rho/ROCK signal that induces cell death of neural cells and neural stem cells and to block the PTEN signal that inhibit the growth of neural stem cells, suggesting that Thiazovivin can inhibit cell death of neural stem cells and increase the ability of neural stem cells to self-renew and grow (Matthias Groszer, et al., Science 294: 2186, 2001). The Thiazovivin is a ROCK (Rho-associated kinase) inhibitor, which selectively inhibit the ROCK. Y27632 or the like can also be used in replace to thiazovivin. A medium is treated with Thiazovivin so as to contain Thiazovivin at an effective concentration. Herein, the effective concentration may vary depending on factors well known in the art, including the kind of medium and a culture method.

"Valproic acid (VPA, 2-propylpentanoic acid)" that is used in the present invention is a histone deacetylase inhibitor that inhibits histone deacetylase, and is known to induce highly acetylated chromatin to promote expression of cell growth inhibitors and genes essential for induction of differentiation to thereby induce differentiation of cells (cancer cells), inhibit angiogenesis, arrest the cell cycle in the G1 phase to induce apoptosis of cancers. Therefore, it indicating that valproic acid has potent cytostatic anticancer activity. It is known that histone deacetylase (HDAC) inhibits gene transcription by pRB/E2F, and disruption of histone acetylation is associated with various carcinogenesis. In addition, it is known that HDAC is highly expressed in poor environmental conditions, including hypoxia, low glucose levels, cellular carcinogenesis, to inhibit expression of cell growth inhibitors to thereby promote cell growth, indicating that HDAC is an important regulator in cellular carcinogenesis and differentiation. In particular, the VPA is known to induce the reduction of inositol, inhibit GSK-3β, activate the ERK pathway, and stimulate the PPAR activity.

In addition to the HDAC inhibitor VPA (Valproic acid, 2-propylpentanoic acid), trichostatin (TSA) or its derivatives may also be used, in which the derivatives include various pharmaceutically acceptable inorganic or organic salts. If the concentration of the VPA in the medium is excessively low, the VPA will hardly be effective, and if the concentration of the VPA is excessively high, the VPA will be toxic. For these reasons, the concentration of the VPA in the medium should be determined depending on the type of cells.

"Purmorphamine" that is used in the present invention is a purine compound known to be involved in the Shh signaling pathway. The Purmorphamine is particularly not limited as long as it can induce a Shh signal, and various derivatives thereof can be used. For example, 2-(1-Naphthoxy)-6-(4-morpholinoanilino)-9-cyclohexylpurin) or the like available commercially in the market can be used. The Purmorphamine can be contained in a medium that is typically used to induce into a neural stem cell-like cells. When the medium contains Purmorphamine that is a Shh analog, there is an advantage in that a gene does not need to be introduced into human fibroblasts in order to produce neural stem cells. The medium is treated with Purmorphamine so as to contain Purmorphamine at an effective concentration. Herein, the effective concentration may vary depending on factors well known in the art, including the kind of medium and a culture method.

"A-8301" that is used in the present invention is a TGF-β type I receptor inhibitor that binds to TGF-β type I receptor to interfere with normal signaling of TGF-β type I (Tojo M et al., Cancer Sci. 96: 791-800, 2005). TGF-β type I (transforming growth factor-β type I) is a multifunctional peptide having various effects on cell proliferation, differentiation and various types of cells. This multifunctionality is known to play a pivotal role in the growth and differentiation of various tissues, including adipocyte formation, myocyte formation, bone cell formation, and epithelial cell differentiation and to inhibit the growth of neural stem cells. In addition to the TGF-β type I receptor inhibitor A-8301, any TGF-β type I receptor inhibitor including SB432542 can be used. The low molecular weight material TGF-β type I receptor inhibitor A-8301 that can be used in the present invention is available commercially in the market or can be manufactured. The proliferation of neural stem cells is promoted by treatment of the inhibitor. A medium is treated with the TGF-β type I receptor inhibitor A-8301 so as to contain the TGF-β type I receptor inhibitor A-8301 at an effective concentration. Herein, the effective concentration may vary depending on factors well known in the art, including the kind of medium and a culture method.

"SB432542" that is in the present invention is a ALK5 (activin receptor-like kinase 5) inhibitor that serves to induce rapid defifferentiation to improve chromosomal stability.

"CHIR99021" that is used in the present invention is a GSK (glycogen synthase kinase) inhibitor that targets GSK1/2 which is an upstream molecule involved in the GSK signaling pathway. The CHIR99021 is an aminopyrimidine derivative. In addition to CHIR99021, any GSK inhibitor can be used.

In the present invention, the medium preferably further includes DZNep (Deazaneplanocin A) or 5-AZA, but is not limited thereto. In addition, the medium preferably further include one or more small-molecule compounds selected from the group consisting of PD0325901, ascorbic acid, PS48, forskolin, and tranylcypromine, but is not limited thereto.

"5-Azacitidine (5-AZA)" that is used in the present invention is named "4-amino-1-β-D-ribofuranosyl-1,3,5-triazin-2 (1H)-one", and is known to have DNA demethylation activity. In addition, the 5-Azacitidine is also known as an antineoplastic drug that exhibits activity for leukemia, lymphoma and various solid tumors. The 5-Azacitidine can be obtained through synthesis by a general chemical synthesis method or is available commercially in the market (e.g., Sigma-Aldrich (St Louis, Mo., USA)).

In the present invention, PD0325901 is one of the MEK/ERK signaling pathway inhibitors, and ascorbic acid is one of the water-soluble vitamins and has a strong antioxidant activity.

In the present invention, forskolin serves to directly activate the catalytic subunit of adenylate cyclase to increase the intracellular concentration of cAMP, and tranylcypromine serves to inhibit monoamine oxidase (MAO), an enzyme that normally degrades norepinephrine in the synaptic cleft.

In the present invention, the culture medium includes any medium that is usually used to culture neural stem cells. The medium used for culture typically includes a carbon source, a nitrogen source, and a trace element component. The medium is preferably made of, but not limited to, DMEM/F12, N2, B27, bFGF (basic fibroblast growth factor), and EGF (epidermal growth factor).

As a medium for culture of induced neural stem cells in the present invention, any basal medium known in the art may be used without limitation. The basal medium that is used in the present invention may be a synthetic basal medium or a commercially available basal medium. Examples of the commercially available basal medium include Dulbecco's modified eagle's medium (DMEM), minimal essential medium (MEM), basal medium eagle (BME), RPMI 1640, F-10, F-12, α-minimal essential medium (α-MEM), Glasgow's minimal essential medium (G-MEM), and Isocove's modified Dulbecco's medium, but is not limited thereto. The commercially available basal medium may be DMEM. In a specific example of the present invention, the induced neural stem cells were cultured in the DMEM medium.

In the present invention, the culture period of the human fibroblasts is preferably 10-15 days, but is not limited thereto.

The method according to the present invention preferably further comprises the steps of: forming spheres by subculturing and then suspension culturing the human fibroblasts; and adherent culturing the formed spheres and then suspension culturing the adherent cultured spheres. However, the scope of the present invention is not limited thereto. Each of the suspension culture and the adherent culture is preferably performed for 7-10 days, and the step of adherent culturing and suspension culturing is repeatedly performed 2 to 4 times, but the scope of the present invention is not limited thereto.

In the present invention, the "neural stem cells" are undifferentiated cells having a self-replicating ability and the ability to differentiate into neurons and/or glia, e.g., astrocytes, oligodendrocytes, and/or Schwann cells. The neural stem cells differentiate into neural cells, for example, neurons or glias via neural progenitor cells or glial progenitor cells, which differentiate into specific neural cells.

In the present invention, the neural stem cells may express nestin, sox1 or musashi1. The neural stem cells may differentiate into one or more selected from the group consisting of astrocytes, oligodendrocytes, neurons, dopaminergic neurons, GABAergic neurons, motor neurons, and cholinergic neurons, but is not limited thereto.

In the present invention, the neural stem cells may maintain chromosomal stability, and may be maintained in an undifferentiated state for more than 10 passages, but the scope of the present invention is not limited thereto.

Most methods that directly covert human fibroblasts into neural stem cells comprise introducing foreign genes that are involved in formation of neural stem cells. Herein, the foreign genes are introduced by various methods. Particularly, a method that is mainly used to introduce the foreign genes employs a lentiviral or retroviral vector system. Introduction of foreign genes into cells using virus may possibly cause genomic instability due to random integration of the foreign genes, and cancer may occur when the cells are clinically applied to patients. For this reason, methods that use small molecules without introducing foreign genes have been suggested. In recent years, studies focused on inducing direct conversion of fibroblasts using various small-molecule compounds have been actively conducted, however, since these studies use at least one gene, it is still impossible to convert human somatic cells into desired neural stem cells without introduction of foreign genes.

However, the technology of the present invention is a method of deriving genetically stable neural stem cells from human fibroblasts without introduction of a foreign gene, and has been designed to overcome the shortcomings of conventional methods that comprises introducing foreign genes and that may induce tumorigenesis.

According to the present invention, human fibroblasts are directly converted into neural stem cells using only a combination of small-molecule compounds. Thus, the present invention overcomes many problems occurring in conventional technologies, for example, ethical issues associated with the use of embryonic stem cells, immune rejection, tumorigenesis caused by the use of embryonic stem cells and induced pluripotent stem cells, etc., and thus neural stem cells obtained according to the present invention have a high potential to be used as cellular therapeutic agents for patients. In addition, neural stem cells obtained directly from the somatic cells of brain disease patients may be used as new cell models to study the mechanisms of diseases caused by neural cell damage or death. Neural stem cells that are produced according to this method are produced in a very rapid and cost-effective manner compared to induced pluripotent stem cells. Namely, the amount of time and cost required to produce induced pluripotent stem cells and to allow the cells to differentiate into neural cells is at least twice larger than that required for the neural stem cells of the present invention.

Furthermore, neural stem cells obtained by cross differentiation according to the present invention have advantages over adult neural stem cells in that they raise no ethical issues, because they do not need to be obtained from fetal or adult brains, and in that they can be produced in desired amounts because the self-renewability thereof is not limited, unlike adult stem cells having a limited ability to self-renew. In addition, because neural stem cells obtained by direct conversion can be obtained from the cells of patient themselves, they have no immune rejection, can be used to produce patient-specific cell models, and can also be used to evaluate the patient-specific toxicity of developed drugs and to develop new drugs. Particularly, because neural stem cells obtained by direct conversion according to the present invention are produced without using a foreign gene, they avoid the risk of tumorigenesis caused by random integration of foreign genes, and thus have a high potential to be used as cellular therapeutic agents.

Therefore, in another aspect, the present invention is directed to a cellular therapeutic agent for treating brain disease, which contains neural stem cells produced by a method comprising a step of culturing human fibroblasts in a medium containing small-molecule compounds.

In the present invention, the brain disease may be stroke, cerebral hemorrhage, cerebral infarction, Alzheimer's disease, dementia, Huntington's disease, Parkinson's disease, multiple sclerosis, multiple system atrophy, epilepsy, Pick's disease, or Creutzfeldt-Jakob disease, but is not limited thereto.

Cells according to the present invention may be clinically applied for treatment of brain diseases. When neural stem cells from patients having genetic brain diseases are produced, these cells may provide brain disease cell models that may be used directly in studies on disease mechanisms. Furthermore, when mutant genes in cells are replaced with normal genes by genetic manipulation, the cells may be used as cellular therapeutic agents for treatment of patients having genetic brain diseases.

As used herein, the term "cellular therapeutic agent" refers to a drug used for the purpose of treatment, diagnosis and prevention, which contains a cell or tissue prepared through isolation from humans, culture and specific operation (as provided by the US FDA). Specifically, it refers to a drug used for the purpose of treatment, diagnosis and prevention of diseases through a series of behaviors of in vitro multiplying and sorting living autologous, allogenic and xenogenic cells or changing the biological characteristics of cells by other means in order to recover the functions of cells and tissues.

As used herein, the term "treatment" refers to any action resulting in improvements in symptoms of diseases or the beneficial alteration of diseases owing to the administration of the cellular therapeutic agent.

The cellular therapeutic agent of the present invention can be administered via any general route as long as it can reach a desired tissue. The cellular therapeutic agent composition of the present invention can be administered parenterally, for example, intraperitoneally, intravenously, intramuscularly, subcutaneously, transdermally, but is not limited thereto.

The cellular therapeutic agent composition can be formulated in a suitable form with a pharmaceutically acceptable carrier that is generally used in the cell therapy. As used herein, the term "pharmaceutically acceptable composition" refers to a composition that is physiologically acceptable and does not cause gastric disorder, allergic reactions such as gastrointestinal disorder or vertigo, or similar reactions, when administered to humans. Examples of the pharmaceutically acceptable carrier include carriers for parenteral administration, such as water, suitable oil, saline solution, aqueous glucose, and glycol. The cellular therapeutic agent composition of the present invention may further comprise a stabilizer and a preservative. Suitable stabilizers include antioxidants, such as sodium bisulphite, sodium sulphite and ascorbic acid. Suitable preservatives include benzalkonium chloride, methyl- or propyl-paraben, and chlorobutanol. Other pharmaceutically acceptable carriers can be found in Remington's Pharmaceutical Sciences, 19th ed., Mack Publishing Company, Easton, Pa., 1995.

In addition, the cellular therapeutic agent of the present invention may be administered by any device that can deliver the cellular therapeutic agent into target cells.

The cellular therapeutic agent composition of the present invention may comprise a therapeutically effective amount of the cellular therapeutic agent for the purpose of treatment of diseases.

As used herein, the term "therapeutically effective amount" is refers to an amount of an active ingredient or a pharmaceutical composition that induces a biological or medical reaction in tissue systems, animals, or humans, and is considered by researchers, veterinarians, doctors, or other clinicians. The therapeutically effective amount comprises an amount of inducing the alleviation of the symptoms of the disease or disorder being treated.

It is obvious to those skilled in the art that cell therapeutic agent contained in the composition of the present invention will be changed according to a desired effect. Therefore, the optimum content of the cell therapeutic agent in the composition of the present invention can be easily determined by those skilled in the art, and may be adjusted depending on various factors including the type and severity of a disease, the contents of other components contained in the composition, the type of formulation, the patient's age, body weight, general health condition, sex and diet, administration time, administration route, the secretion rate of the composition, duration of treatment, and concurrently used medications. It is important that the cellular therapeutic agent according to the present invention should contain the neural stem cells in an amount that can exhibit the maximum effect without causing side effects. This amount should be determined in consideration of the factors. For example, the daily dose of the neural stem cells according to the present invention may be $1.0 \times 10^4$ to $1.0 \times 10^{10}$ cells/kg body weight, preferably $1.0 \times 10^5$ to $1.0 \times 10^9$ cells/kg body weight, which may be administered once or in several divided portions a day. However, it is to be understood that the actual dose of the active ingredient should be determined in consideration of various relevant factors, including the disease to be treated, the severity of the disease, the route of administration, and the patient's body weight, age and sex. Thus, the dose does not limit the scope of the present invention in any way.

In addition, in the treatment method of the present invention, a composition comprising the cellular therapeutic agent of the present invention as an active ingredient can be administered in a conventional manner via an intrarectal, intravenous, intra-arterial, intraperitoneal, intramuscular, intrasternal, transdermal, topical, intraocular or intradermal route.

The present invention provides a method for treating brain disease, comprising administering a therapeutically effective amount of the cellular therapeutic agent of the present invention to mammals. As used herein, the term "mammals" refers to mammals that are the objects of treatment, observation or experiment, preferably humans.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Investigation of Functions of Small-Molecule Compounds and Combination Thereof 1-1: Investigation of Functions of Small-Molecule Compounds To convert human fibroblasts into neural stem cells, 13 different small-molecule compounds related to reprogramming were selectively sorted and used (Table 1).

Figure 2:
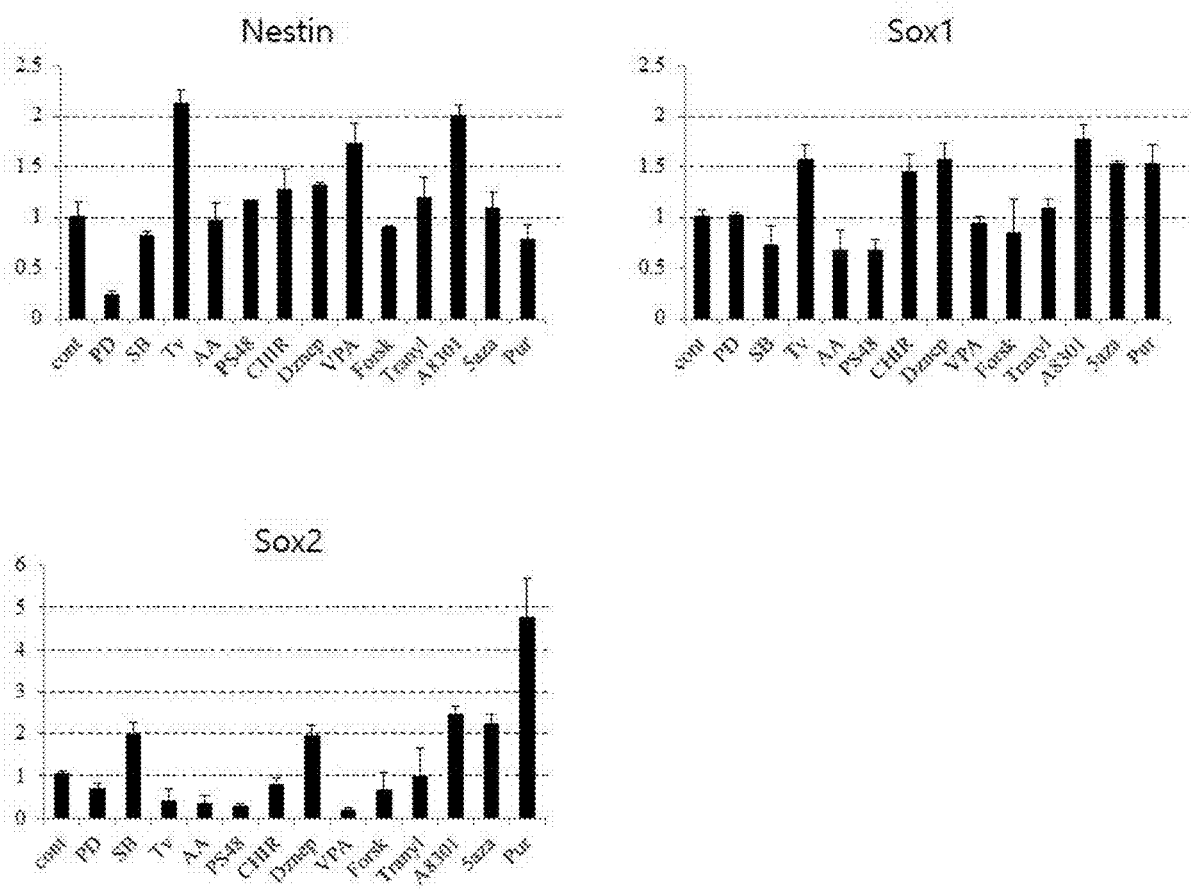
FIG. 2 shows the results of analyzing gene expressions following addition of 13 small-molecule compounds.

(snail, N-cadherin, E-cadherin), endodermal and mesodermal markers (AFP, GATA4), and a marker (Zsacn4) associated with the maintenance of chromosomal stability, in the cell sample, were analyzed by quantitative PCR (FIG. 2).

As a result, it was shown that 8 different small-molecule compounds (Thiazovivin, Valproic acid, Purmorphamine, A8301, SB431542, CHIR99021, Deazaneplanocin A, and 5-AZA) distinctly increased expressions of the neural stem cell marker genes.

1-2: Combination of Small-Molecule Compounds

In order to determine the most efficient conditions for production of neural stem cells, various media obtained by removing each small-molecule compound from a medium containing all the 8 different small-molecule compounds identified in Example 1-1 were used to examine whether fibroblasts would be converted into neural stem cells in each of the media. Briefly, $1 \times 10^5$ human fibroblasts were prepared in 60 mm dishes, and then the morphological changes of the cells were observed while the medium was replaced at 2-3-day intervals with each of various media as shown in Table 2 below. In addition, the cells were sampled while they were subcultured, and the expression patterns of various genes in the cell samples were analyzed.

TABLE 1

| # | Name | Formal Name |
|---|------|-------------|
| 1 | PD0325901 | N-[(2R)-2,3-dihydroxypropoxy]-3,4-difluoro-2-[(2-fluoro-4-iodophenyl)amino]-benzamide |
| 2 | SB431542 | 4-[4-(3,4-Methylenedioxyphenyl)-5-(2-pyridyl)-1H-imidazol-2-yl]benzamide |
| 3 | Thiazovivin | N-(phenylmethyl)-2-(4-pyrimidinylamino)-4-thiazolecarboxamide |
| 4 | Ascorbic acid | R)-5-((S)-1,2-dihydroxyethyl)-3,4-dihydroxyfuran-2(5H)-one |
| 5 | PS48 | 5-(4-chlorophenyl)-3-phenyl-2Z-pentenoic acid |
| 6 | CHIR99021 | 6-[[2-[[4-(2,4-dichlorophenyl)-5-(5-methyl-1H-imidazol-2-yl)-2-pyrimidinyl]amino]ethyl]amino]-3-pyridinecarbonitrile |
| 7 | DZNep (3-Deazaneplanocin A) | 5R-(4-amino-1H-imidazo[4,5-c]pyridin-1-yl)-3-(hydroxymethyl)-3-cyclopentene-1S,2R-diol |
| 8 | Valproic acid | 2-propyl-pentanoic acid |
| 9 | Forskolin | 5-(acetyloxy)-3-ethenyldodecahydro-6,10,10b-trihydroxy-3,4a,7,7,10a-pentamethyl-(3R,4aR,5S,6S,6aS,10S,10aR,10bS)-1H-Naphtho[2,1-b]pyran-1-one |
| 10 | Tranylcypromine | (1R.2S)--2-phenyl-cyclopropanamine, monohydrochloride |
| 11 | A8301 | 3-(6-Methyl-2-pyridinyl)-N-phenyl-4-(4-quinolinyl)-1H-pyrazole-1-carbothioamide |
| 12 | 5-AZA | |
| 13 | Purmorphamine | 9-cyclohexyl-N-[4-(morpholinyl)phenyl]-2-(1-naphthalenyloxy)-9H-purin-6-amine |

To investigate the function of each of small-molecule compounds and find an optimal combination of small-molecule compounds, $1 \times 10^5$ human fibroblasts were prepared in 60 mm dishes, and on the next day, the cells were cultured in a neurobasal medium (containing DMEM/F12, N2, B27, bFGF, and EGF) supplemented with each of 13 different small-molecule compounds (PD0325901, SB431542, Thiazovivin, Ascorbic acid, PS48, CHIR99021, Deazaneplanocin A, Valproic acid, Forskolin, Tranylcypromine, A8301, 5-AZA, and Purmorphamine). Then, the morphological changes of the cells were observed while the medium was replaced at 2-3-day intervals (FIG. 1). The cells were subcultured at 5-day intervals, and in this stage, the cells were sampled in order to examine gene expression patterns therein. Using the cell sample, the expression patterns of a fibroblast marker (Thy1), neural stem cell markers (nestin, sox1, sox2, pax6), a MET or EMT marker

TABLE 2

DMEM/F12 + N2, B27, bFGF, EGF (NSC basal medium)

| | Chemicals |
|---|---|
| Condition 1 | Without chemicals |
| Condition 2 | VPA, Purmor, A8301, SB, CHIR, DZNep, 5-AZA |
| Condition 3 | TV, Purmor, A8301, SB, CHIR, DZNep, 5-AZA |
| Condition 4 | TV, VPA, A8301, SB, CHIR, DZNep, 5-AZA |
| Condition 5 | TV, VPA, Purmor, SB, CHIR, DZNep, 5-AZA |
| Condition 6 | TV, VPA, Purmor, A8301, CHIR, DZNep, 5-AZA |
| Condition 7 | TV, VPA, Purmor, A8301, SB, DZNep, 5-AZA |
| Condition 8 | TV, VPA, Purmor, A8301, SB, CHIR, 5-AZA |
| Condition 9 | TV, VPA, Purmor, A8301, SB, CHIR, DZNep |
| Condition 10 | TV, VPA, Purmor, A8301, SB, CHIR, DZNep, 5-AZA |

As a result, combinations of 6 small-molecule compounds (Thiazovivin, Valproic acid, Purmorphamine, SB431542, and CHIR99021) to 8 small-molecule compounds (Thiazovivin, Valproic acid, Purmorphamine, A8301, SB431542, CHIR99021, Deazaneplanocin A, and 5-AZA), confirmed to increase expressions of the neural stem cell marker genes, were selected. Thus, it was found that the use of only 6 to 8 small-molecule compounds could convert human fibroblasts into neural stem cells. In addition, it was shown that the time point at which cells having a morphology similar to that of neural stem cells were found did differ depending on the origin thereof, even though they were produced from the same human fibroblasts.

Example 2: Derivation of Neural Stem Cells from Human Fibroblasts and Culture Thereof As a combination of small-molecule compounds required to convert human fibroblasts into neural stem cells was determined, it was attempted to establish conditions for stable derivation of neural stem cells and culture. In addition, in order to examine the efficiency with which human fibroblasts are converted into neural stem cells, comparison was performed using media supplemented with at least 4 small-molecule compounds. Briefly, 1×10$^5$ cells were prepared, and then cultured in three different media obtained by adding 4 small-molecule compounds (Thiazovivin, Valproic acid, Purmorphamine, and A8301), 6 small-molecule compounds (Thiazovivin, Valproic acid, Purmorphamine, A8301, SB431542, and CHIR99021), or 8 small-molecule compounds (Thiazovivin, Valproic acid, Purmorphamine, A8301, SB431542, CHIR99021, Deazaneplanocin A, and 5-AZA) to a neurobasal medium containing DMEM/F12, N2, B27, bFGF and EGF.

As a result, it was observed that the morphology of the cells started to change slowly from about 3 days after the start of derivation. On about 7-10 days, in the medium supplemented with 4 different small-molecule compounds, the morphology of the cells did not significantly differ from that of the fibroblasts, but in the medium supplemented with 6 or 8 different small-molecule compounds, cells having a morphology similar to that of neural stem cells were formed.

Figure 3:
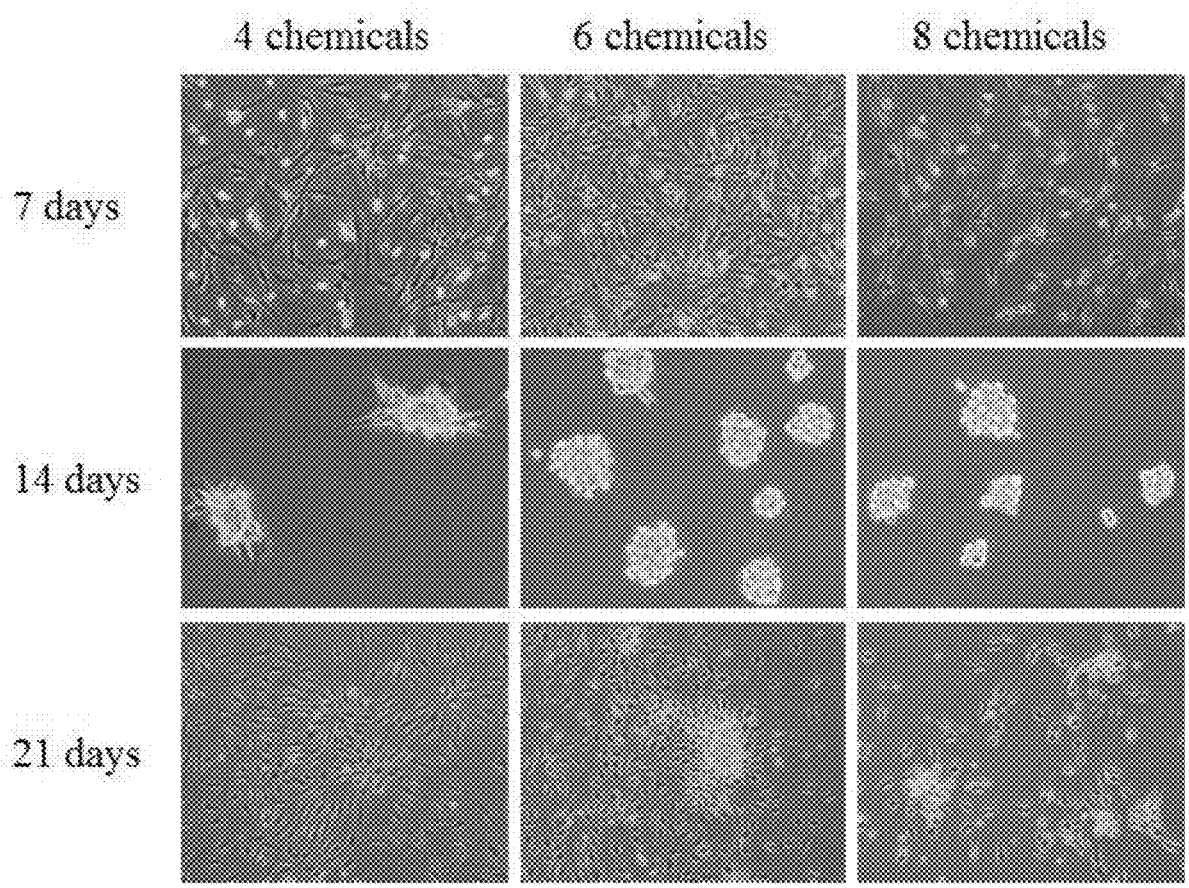
FIG. 3 shows the results of observing cellular morphological changes following the use of 4, 6 and 8 different small-molecule compounds.

Next, the cells were subcultured and subjected to suspension culture using a Petri dish in order to improve the properties of neural stem cells. 7-10 days after suspension culture, the cells mostly formed small spheres in the medium supplemented with 6 or 8 different small-molecule compounds. However, in the medium supplemented with 4 small-molecule compounds, spheres were not properly formed. The formed small spheres were adhered to a PLO/FN-coated dish and further cultured for about 7-10 days. It could be seen that the morphology of the cells in this stage was more similar to that of neural stem cells (FIG. 3). When suspension culture and adherent culture were repeatedly performed 2-4 times, the morphology of the cells in the medium supplemented with 6 or 8 different small-molecule compounds more clearly changed. However, in the medium supplemented with 4 different small-molecule compounds, the morphology of the cells did not change despite repeated cultures. Neural stem cells derived by the medium supplemented with 6 or 8 different small-molecule compounds as described above maintained the morphology of neural stem cells, even when these cells were cultured for a long period of time together with continuous subculture.

Figure 4:
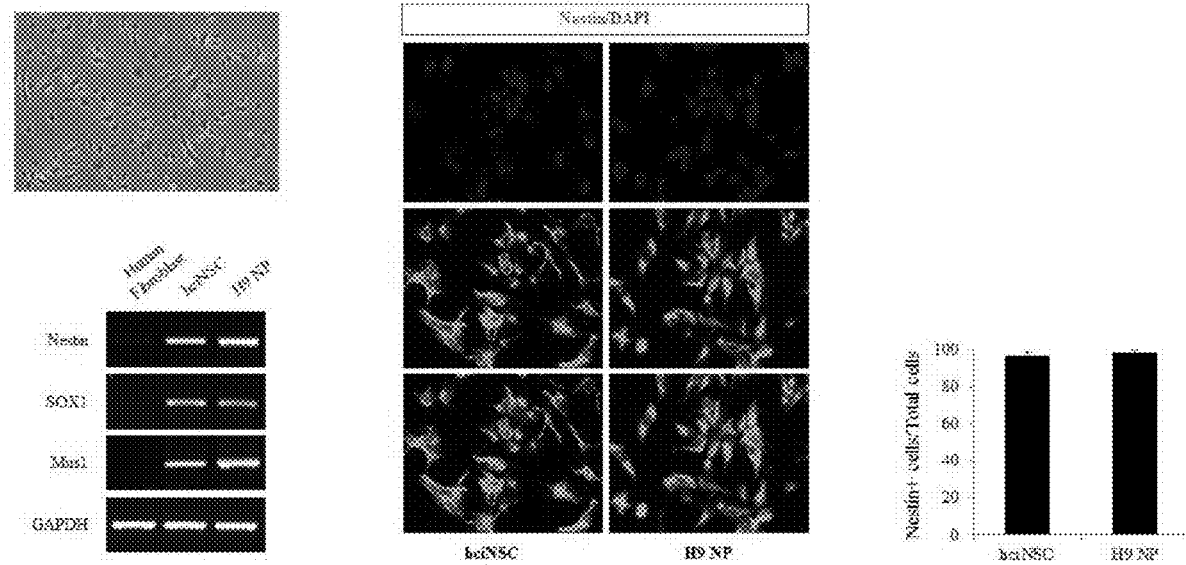
FIG. 4 shows the results of observing morphology, marker genes and protein expressions in fibroblast-derived neural stem cells.

Example 3: Characterization of Neural Stem Cells Derived by Small-Molecule Compounds Examination was made of whether the human neural stem cells derived by DMEM/F12+N2B27 supplemented with 6 different small-molecule compounds show the general characteristics of neural stem cells. Briefly, PCR and immunocytochemistry (ICC) staining were performed in order to examine whether the neural stem cells would express neural stem cell markers. The results of immunocytochemistry (ICC) staining indicated that the neural stem cells expressed nestin, and the results of PCR indicated that the expression levels of neural stem cell markers (nestin, sox1, and musashi1) in the neural stem cells derived from fibroblasts were similar to those in neural stem cells derived from human embryonic stem cells (FIG. 4).

Figure 5:
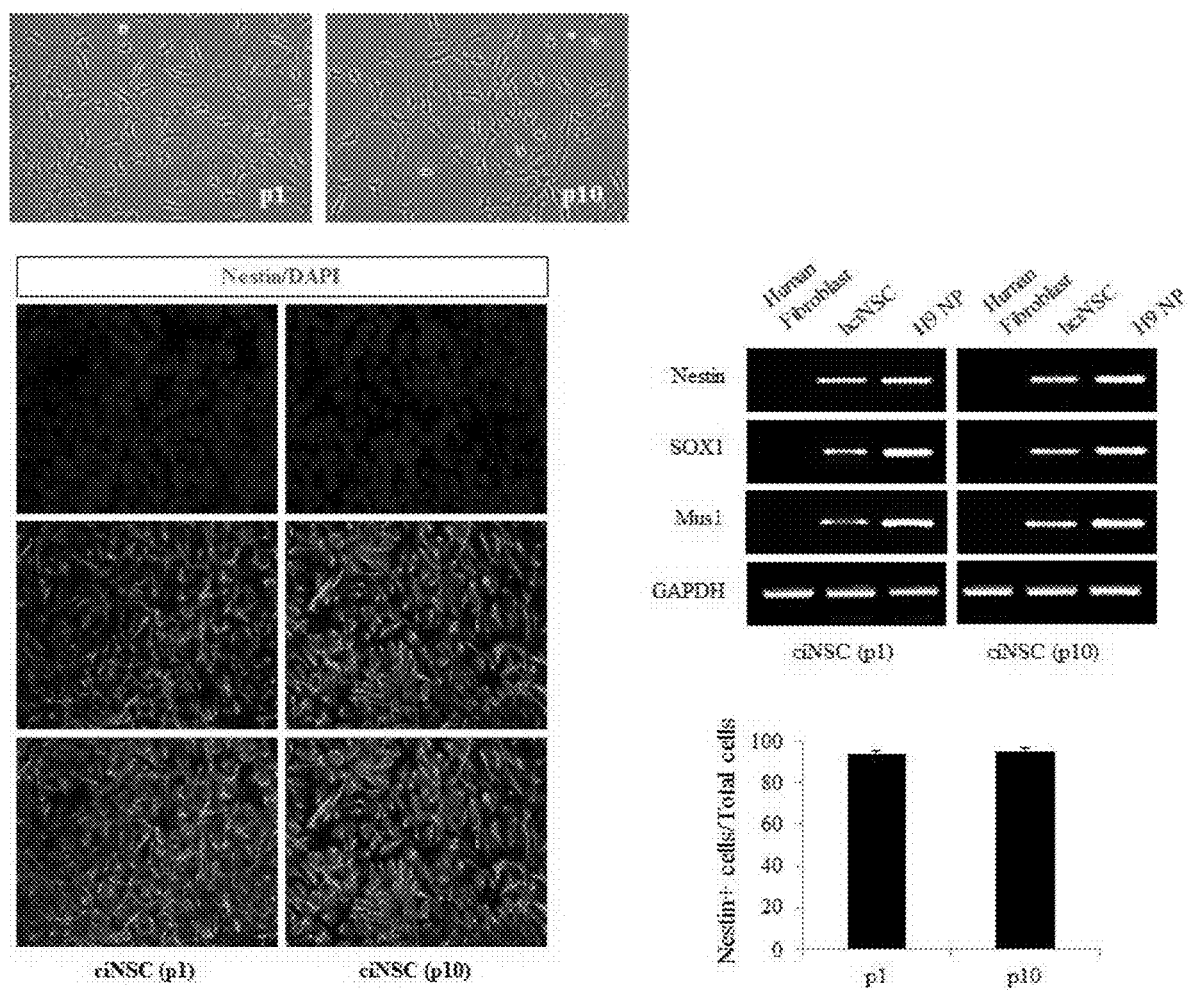
FIG. 5 shows the results of observing morphology, marker genes and protein expressions in fibroblast-derived neural stem cells in initial and late stages.
Figure 6:
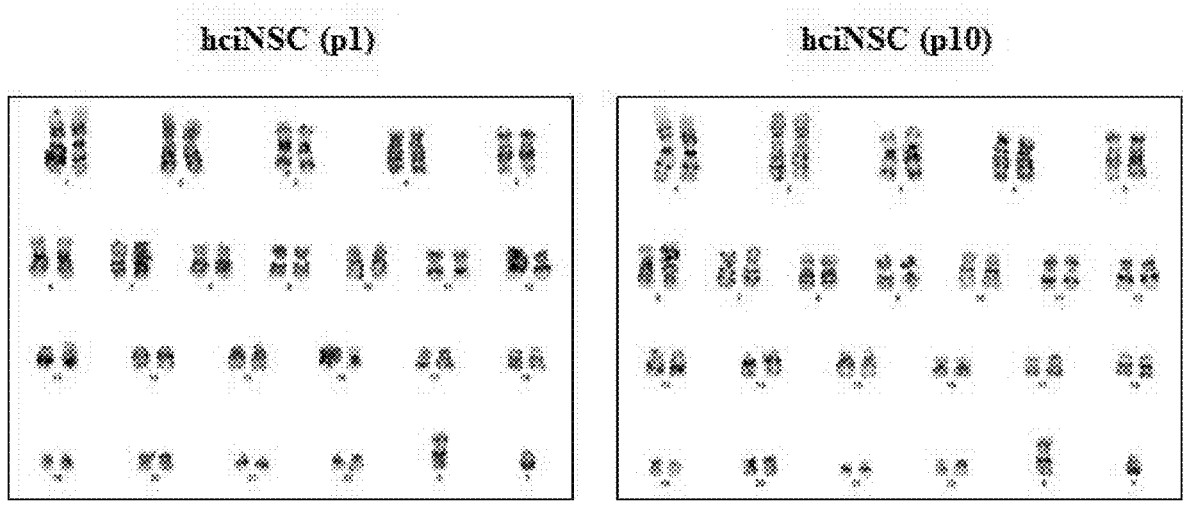
FIG. 6 shows the results of analyzing chromosomes in fibroblast-derived neural stem cells by karyotype analysis.
Figure 7:
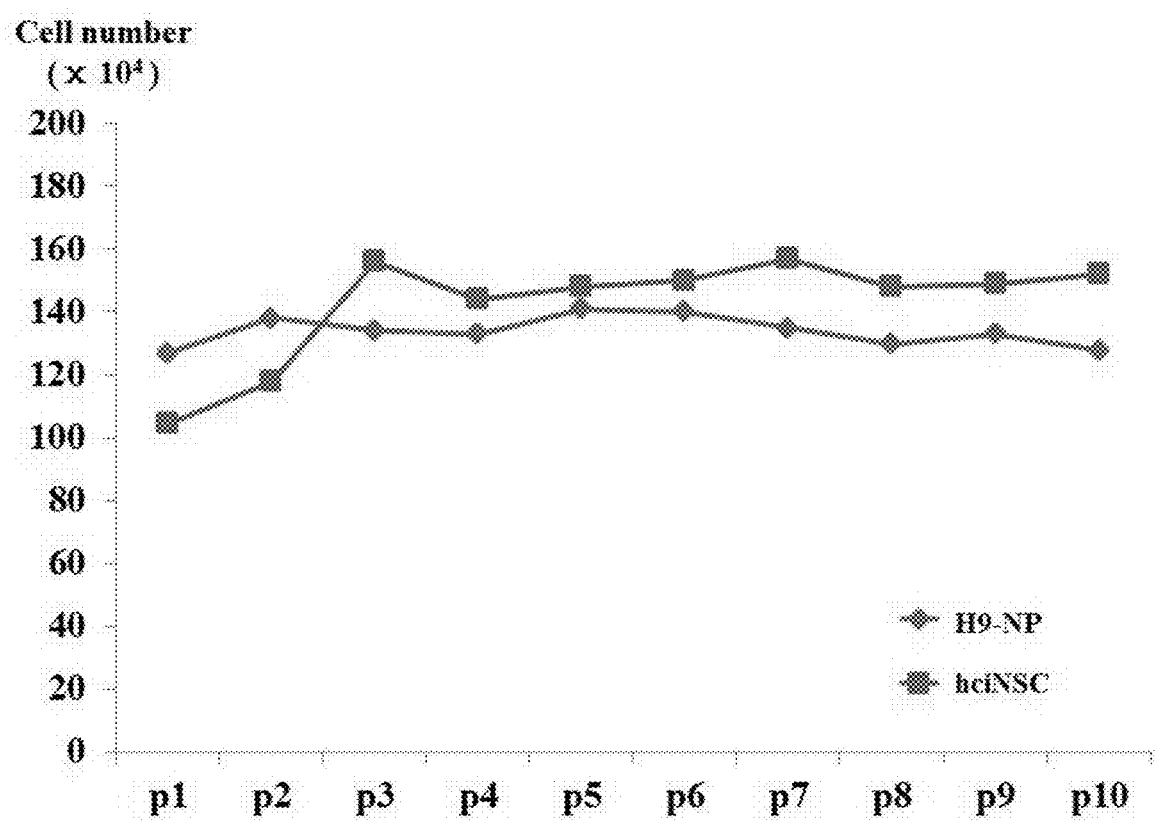
FIG. 7 shows the results of analyzing the growth rate of fibroblast-derived neural stem cells as a function of time.

In order to examine whether the properties of the fibroblast-derived neural stem cells would be maintained during long-term culture, the morphology of the cells in each of the initial and late stages was observed. Furthermore, expression of nestin was analyzed by immunocytochemistry (ICC) staining, and expressions of neural stem cell markers (nestin, sox1, and musashi1) were analyzed by PCR (FIG. 5). In addition, whether or not chromosomes in the fibroblast-derived neural stem cells in the initial and late stages would be abnormal was analyzed by chromosomal analysis (FIG. 6), and the growth rate of the fibroblast-derived neural stem cells during growth and culture was compared with that of neural stem cells derived from human embryonic stem cells (FIG. 7). As a result, it was shown that the fibroblast-derived neural stem cells maintained the morphology and properties of neural stem cells even during long-term culture and, at the same time, could be continuously cultured without chromosomal abnormality.

Figure 8:
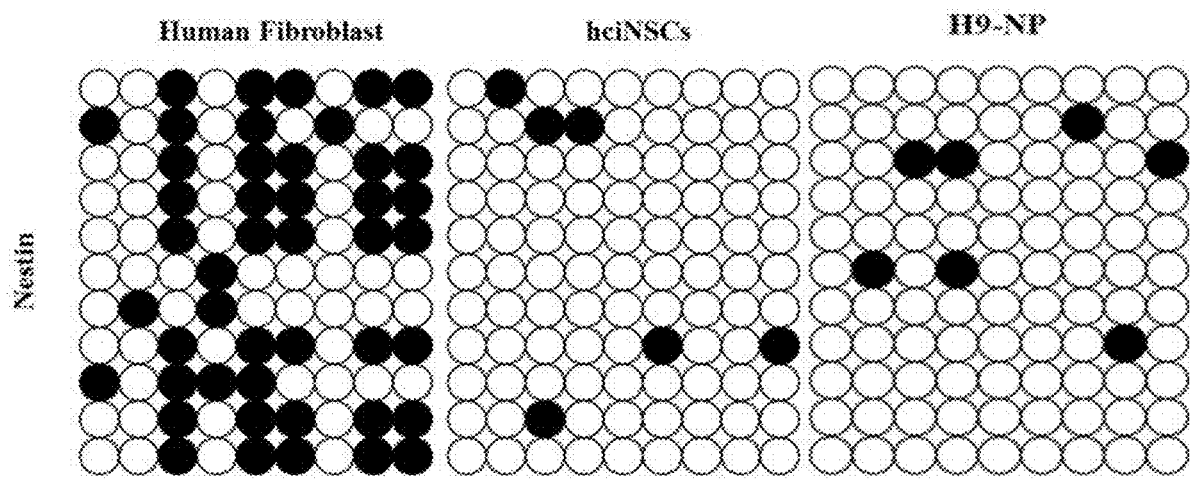
FIG. 8 shows the results of analyzing the epigenetic change of fibroblast-derived neural stem cells by bisulfite PCR analysis.

Next, in order to examine the epigenetic change of the fibroblast-derived neural stem cells, whether the promoter region of the neural stem cell marker nestin would be methylated/acetylated was analyzed by bisulfite PCR. As a result, it could be seen that the characteristics of the fibroblasts completely changed to the characteristics of neural stem cells (FIG. 8).

Example 4: Examination of In Vitro Differentiation Potential of Fibroblast-Derived Human Neural Stem Cells The results of Examples 1 to 3 indicated that the derivation of neural stem cells from fibroblasts was successfully achieved by the use of small-molecule compounds. More specifically, in order to examine the characteristics and usefulness of the fibroblast-derived neural stem cells, the in vitro differentiation potential of the cells was examined. Briefly, the differentiation of the fibroblast-derived neural stem cells into three major types of neural cells (astrocytes, oligodendrocytes and neurons) was performed.

Figure 9:
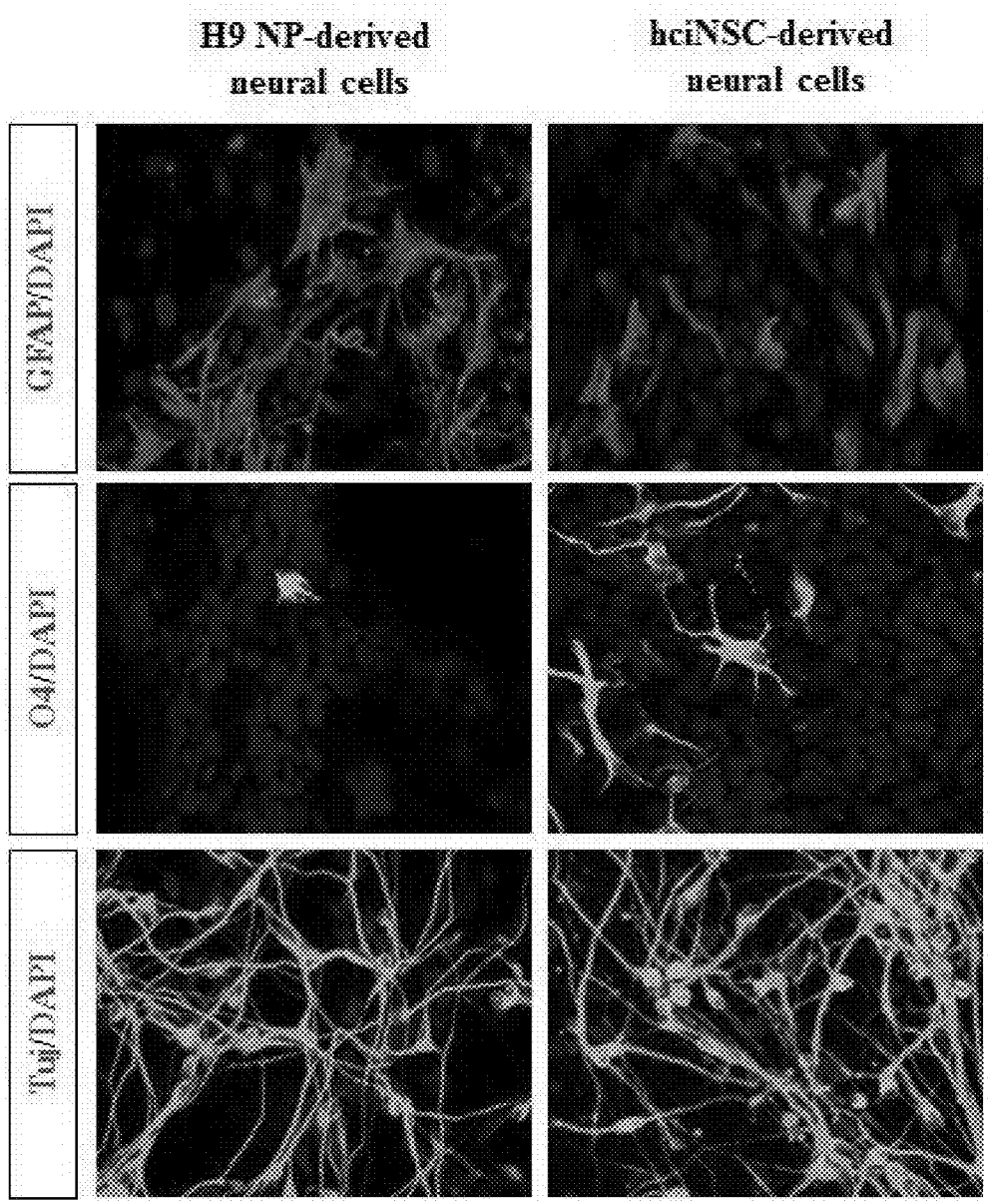
FIG. 9 shows the results of examining the differentiation of fibroblast-derived neural stem cells into three major types of neural cells.

As a result, it was shown that the neural stem cells derived by the small-molecule compounds successfully differentiated into three major types of neural cells (FIG. 9).

Figure 10:
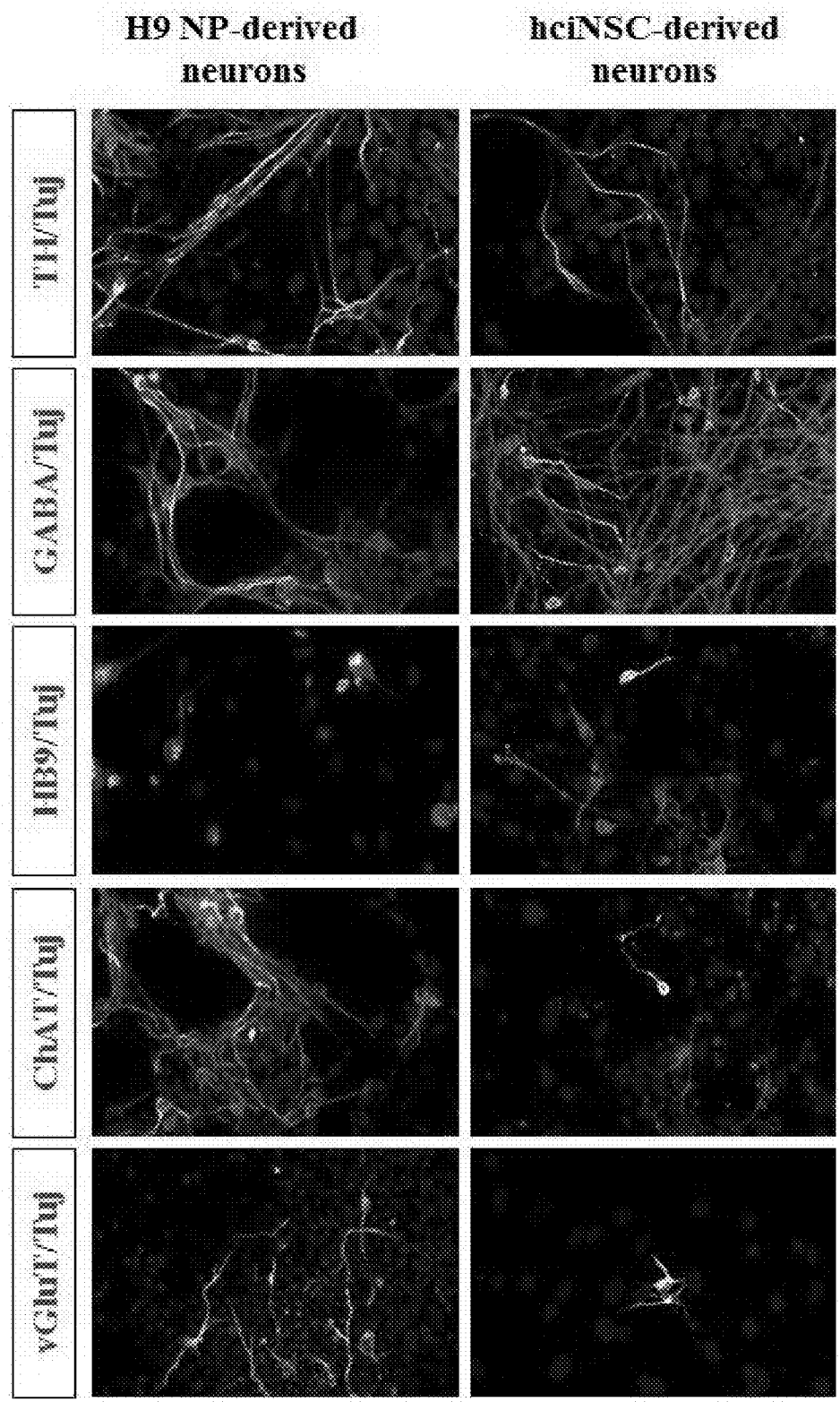
FIG. 10 shows the results of examining the differentiation of fibroblast-derived neural stem cells into various types of neural cells.

Next, whether the fibroblast-derived neural stem cells would differentiate into various types of neural cells was examined. As a result, it was shown that the neural stem cells differentiated into dopaminergic neurons, GABA neurons, motor neurons, cholinergic neurons, and glutamate neurons (FIG. 10). This suggests that the human neural stem cells derived according to the present invention is capable of differentiating into various types of neural cells.

The derivation of human neural stem cells from human fibroblasts, the growth of the neural stem cells, and the potential of the neural stem cells to differentiate into various kinds of functional neural cells, indicate that the human neural stem cells have a very high potential to be used as cellular therapeutic agents for treatment of human brain diseases.

Example 5: Examination of In Vivo Differentiation Potential of Fibroblast-Derived Human Neural Stem Cells The in vitro results in Examples 3 and 4 indicated that the neural stem cells derived from human fibroblasts using the small-molecule compounds could successfully differentiate into three major types of neural cells.

Thus, in order to observe the in vivo differentiation potential of the neural stem cells derived from human fibroblasts using the small-molecule compounds and whether the neural stem cells would be tumorigenic, the fibroblast-derived human neural stem cells were transplanted into the brains of mice (Balb/c, Orient Bio). Next, the mice transplanted with the human neural stem cells were continuously observed for 3 to 7 months.

Figure 11:
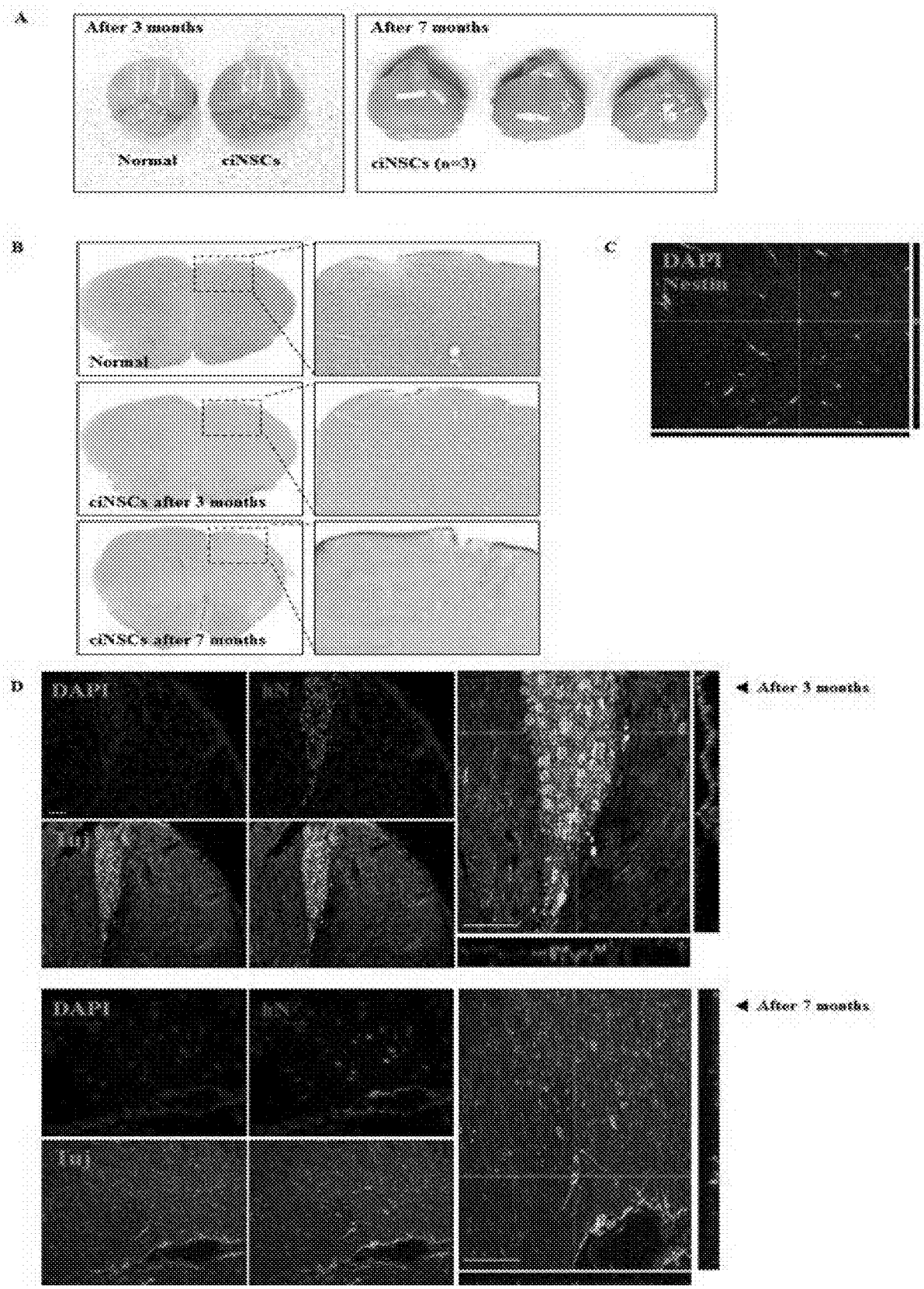
FIGS. 11A through 11D show the results of analyzing the brains of mice transplanted with fibroblast-derived neural stem cells.

As a result, tumorigenesis in the mouse brains transplanted with the human neural stem cells was not apparently observed for 3 to 7 months (FIG. 11A), and H&E (Haematoxylin and Eosin) staining of the brain tissue showed that no tumorigenesis was observed (FIG. 11B). Furthermore, it was shown that the fibroblast-derived neural stem cells expressed a neural stem cell marker, indicating that these cells were successfully transplanted (FIG. 11C). In addition, after 3 to 7 months after transplantation, it was observed that the fibroblast-derived neural stem cells expressed a human cell-specific marker and a neural cell-specific marker, indicating that the transplanted cells differentiated into neural cells (FIG. 11D). This suggests that the human neural stem cells derived by the small-molecule compounds can differentiate into neural cells without tumorigenesis after transplantation.

Such fibroblast-derived neural stem cells can be used as optimal cell models to study neural cell development and brain disease mechanisms, and have a very high potential to be used as cellular therapeutic agents for treatment of human brain diseases, because they are not tumorigenic.

INDUSTRIAL APPLICABILITY

As described above, the method of directly converting human fibroblasts into neural stem cells using small-molecule compounds without introduction of a foreign gene makes it possible to obtain genetically stable neural stem cells in an amount sufficient for use in cell therapy. The neural stem cells obtained according to the method of the present invention can differentiate into functional neural cells and are not tumorigenic. Thus, these neural stem cells are useful as cellular therapeutic agents for treatment of brain diseases.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for producing neural stem cells, the method comprising:
   culturing human fibroblasts in a medium comprising Thiazovivin, Valproic acid, Purmorphamine, A8301, SB431542, CHIR99021, DZNep(Deazaneplanocin A), and 5-AZA.

2. The method of claim 1, wherein the medium further comprises one or more small-molecule compounds selected from the group consisting of PD0325901, ascorbic acid, PS48, forskolin, and tranylcypromine.

3. The method of claim 1, wherein the medium is a DMEM/F12 containing N2, B27, bFGF, and EGF.

4. The method of claim 1, wherein the human fibroblasts are cultured for 10-15 days.

5. The method of claim 1, further comprising the steps of:
   forming spheres by subculturing and then suspension culturing the human fibroblasts; and
   adherent culturing the formed spheres and then suspension culturing the adherent cultured spheres.

6. The method of claim 5, wherein the suspension culture and the adherent culture are each performed for 7-10 days.

7. The method of claim 5, wherein the step of adherent culturing and suspension culturing is repeatedly performed 2 to 4 times.

8. The method of claim 1, wherein the neural stem cells express nestin, sox1 or musashi1.

9. The method of claim 1, wherein the neural stem cells differentiate into one or more selected from the group consisting of astrocytes, oligodendrocytes, neurons, dopaminergic neurons, GABAergic neurons, motor neurons, and cholinergic neurons.

10. The method of claim 1, wherein the neural stem cells maintain chromosomal stability.

11. The method of claim 1, wherein the neural stem cells are maintained in an undifferentiated state for more than 10 passages.

* * * * *